(12) United States Patent
Raman et al.

(10) Patent No.: US 9,085,509 B2
(45) Date of Patent: Jul. 21, 2015

(54) PROCESS FOR PREPARING FESOTERODINE

(75) Inventors: Jayaraman Venkat Raman, Vadodara (IN); Samir Patel, Vadodara (IN); Indrajit Thakor, Vadodara (IN); Mahesh Ladani, Vadodara (IN); Chetan Patil, Vadodara (IN); Ronak Patel, Vadodara (IN); Prashant Raval, Vadodara (IN); Viral Parekh, Vadodara (IN); Hiral Shah, Vadodara (IN)

(73) Assignee: ALEMBIC PHARMACEUTICALS LIMITED, Vadodara, Gujarat (IN)

( * ) Notice: Subject to any disclaimer, the term of this patent is extended or adjusted under 35 U.S.C. 154(b) by 0 days.

(21) Appl. No.: 14/110,175

(22) PCT Filed: Nov. 11, 2011

(86) PCT No.: PCT/IB2011/055039
§ 371 (c)(1),
(2), (4) Date: Oct. 15, 2013

(87) PCT Pub. No.: WO2012/137047
PCT Pub. Date: Oct. 11, 2012

(65) Prior Publication Data
US 2014/0039216 A1 Feb. 6, 2014

(30) Foreign Application Priority Data
Apr. 7, 2011 (IN) .................. 1172/MUM/2011

(51) Int. Cl.
C07C 69/00 (2006.01)
C07C 227/36 (2006.01)
C07B 57/00 (2006.01)
C07C 213/08 (2006.01)
C07C 217/56 (2006.01)
C07C 219/28 (2006.01)
C07C 57/15 (2006.01)
C07C 217/62 (2006.01)

(52) U.S. Cl.
CPC .............. *C07C 227/36* (2013.01); *C07B 57/00* (2013.01); *C07C 57/15* (2013.01); *C07C 213/08* (2013.01); *C07C 217/56* (2013.01); *C07C 217/62* (2013.01); *C07C 219/28* (2013.01)

(58) Field of Classification Search
CPC .. C07C 213/08; C07C 217/56; C07C 217/62; C07C 219/28; C07C 227/36; C07C 57/15
See application file for complete search history.

(56) References Cited

FOREIGN PATENT DOCUMENTS

| CN | 200610029492.2 | * | 1/2006 |
| EP | 2281801 A1 | | 2/2011 |
| WO | 2009/126844 A2 | | 10/2009 |

OTHER PUBLICATIONS

CN2006 description translation 2006.*
International Search Report for PCT/IB2011/055039 dated Jun. 18, 2012 (3 pages).
Writte Opinion for PCT/IB2011/055039 dated Jun. 18, 2012 (5 pages).

* cited by examiner

*Primary Examiner* — Yevegeny Valenrod
*Assistant Examiner* — Blaine G Doletski
(74) *Attorney, Agent, or Firm* — Schiff Hardin LLP

(57) ABSTRACT

The present invention relates to an improved process for the preparation of Fesoterodine and pharmaceutically acceptable salts thereof. The present invention particularly relates to a process for the preparation of fesoterodine and pharmaceutically acceptable salts thereof which involves use and preparation of R(+)benzyl tolterodine and fumarate salt of R(+)-[4-benzyloxy-3-(3-diisopropylamino-1-phenylpropyl)-phenyl]-methanol.

16 Claims, No Drawings

PROCESS FOR PREPARING FESOTERODINE

FIELD OF THE INVENTION

The present invention relates to an improved, commercially viable and industrially advantageous process for the preparation of Fesoterodine or a pharmaceutically acceptable salt thereof in high yield and purity. More specifically the present invention relates to an improved and industrially advantageous optical resolution method of racemic benzyl tolterodine and also relates to novel intermediate compounds, their preparation and use in the process for preparation of Fesoterodine and its related compound.

BACKGROUND OF THE INVENTION

Fesoterodine is [2-[(1R)-3-(Di(propan-2-yl)amino)-1-phenylpropyl]-4-(hydroxymethyl)phenyl]2-methylpropanoate and represented by formula (I).

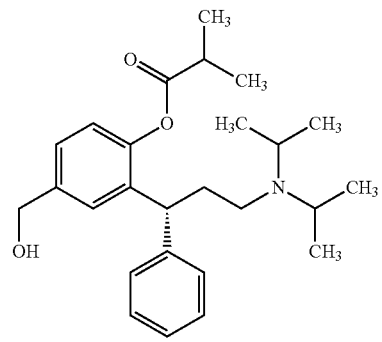

(I)

The product is marketed in the form of fumarate salt. The current pharmaceutical product containing this drug is being sold by Pfizer using the trade name Toviaz, in the form of extended release oral tablets. Fesoterodine is cholinergic antagonist and muscarinic antagonist. Fesoterodine is rapidly de-esterified to its active metabolite, (R)-2-(3-diisopropylamino-1-phenylpropyl)-4-hydroxymethyl-phenol, or 5-hydroxy methyl tolterodine, which is a muscarinic receptor antagonist. Fesoterodine is used as Urinary Incontinence Products. It is used to treat overactive bladder.

Few processes for the synthesis of 3,3-diphenylpropylamine derivatives have been described in the literature.

Tolterodine and other 3,3-diphenylpropylamine analogs were first described in U.S. Pat. No. 5,382,600. Said patent described several methods for preparing tolterodine and its analogs generally based a process for the preparation of Tolterodine which is shown in the Scheme-I.

Scheme-I

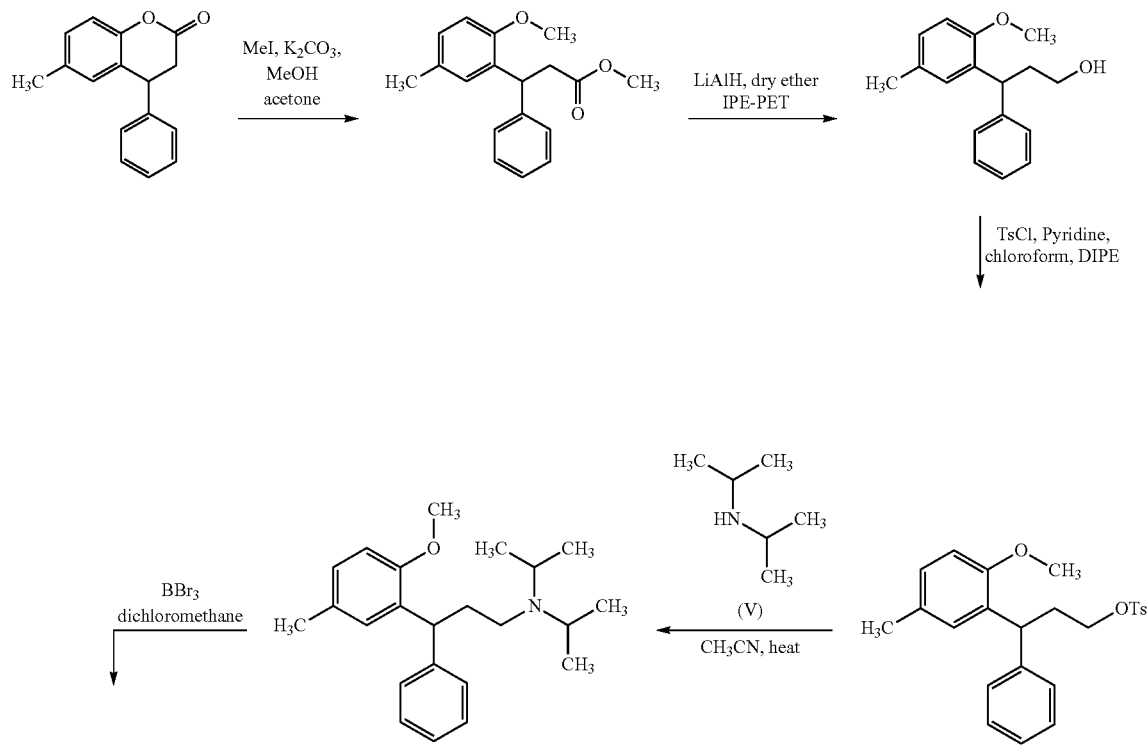

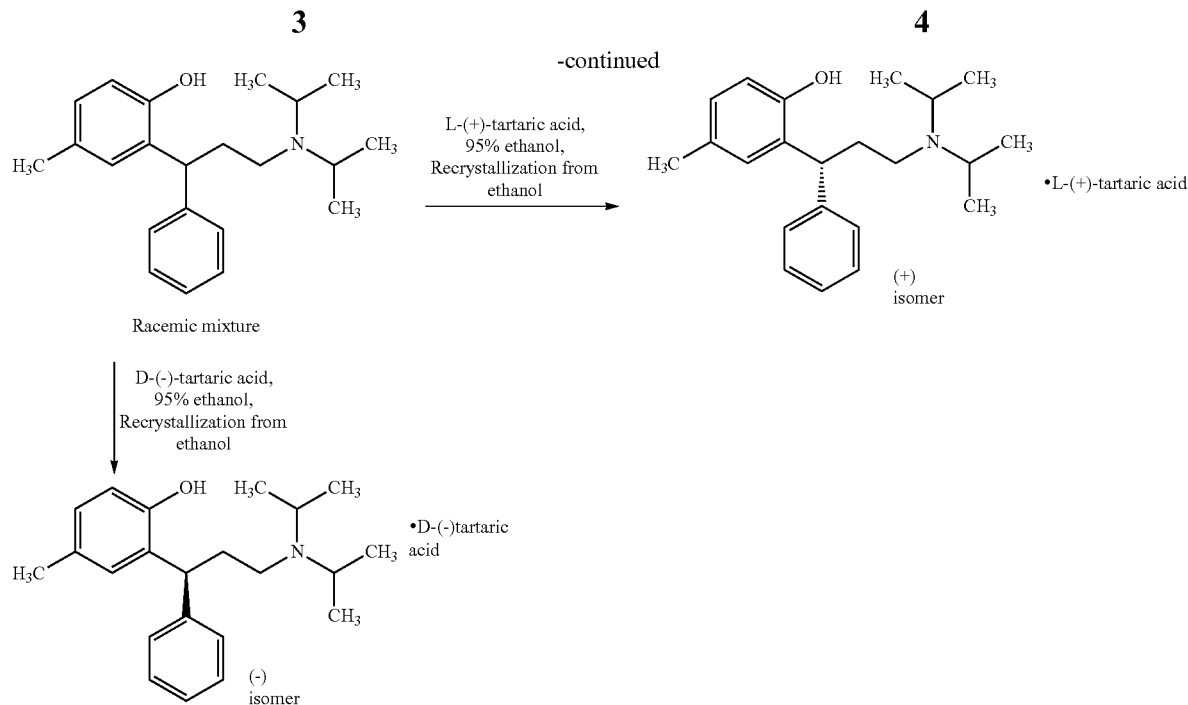

The main problem associated with this process is that it involves use of less economical reagent and which requires specific handling skill when used. Moreover, some of the reagents like Lithium aluminum hydride should be avoided while using at plant because it hazardously reacts towards water and being more hygroscopic in nature compared to other reducing reagents like sodium borohydride. Further use of pyridine is some time prone to hazardous and biologically nondegradable and therefore it is not environment friendly.

Further use of boron tribromide is also non appropriate. All these drawbacks make the process less economical and unsuitable at industrial level.

U.S. Pat. No. 6,713,464 disclosed a variety of 3,3-diphenylpropylamine derivatives, processes for their preparation, pharmaceutical compositions in which they are present and method of use thereof. A process for the preparation of Fesoterodine which is shown in the Scheme-II.

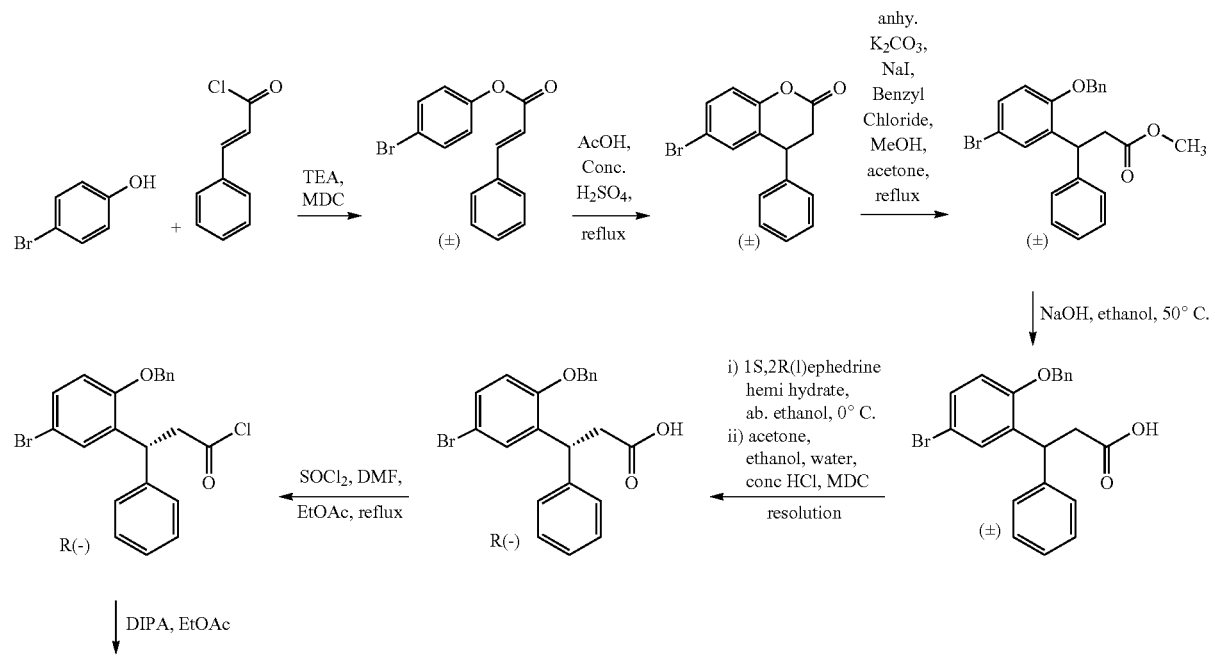

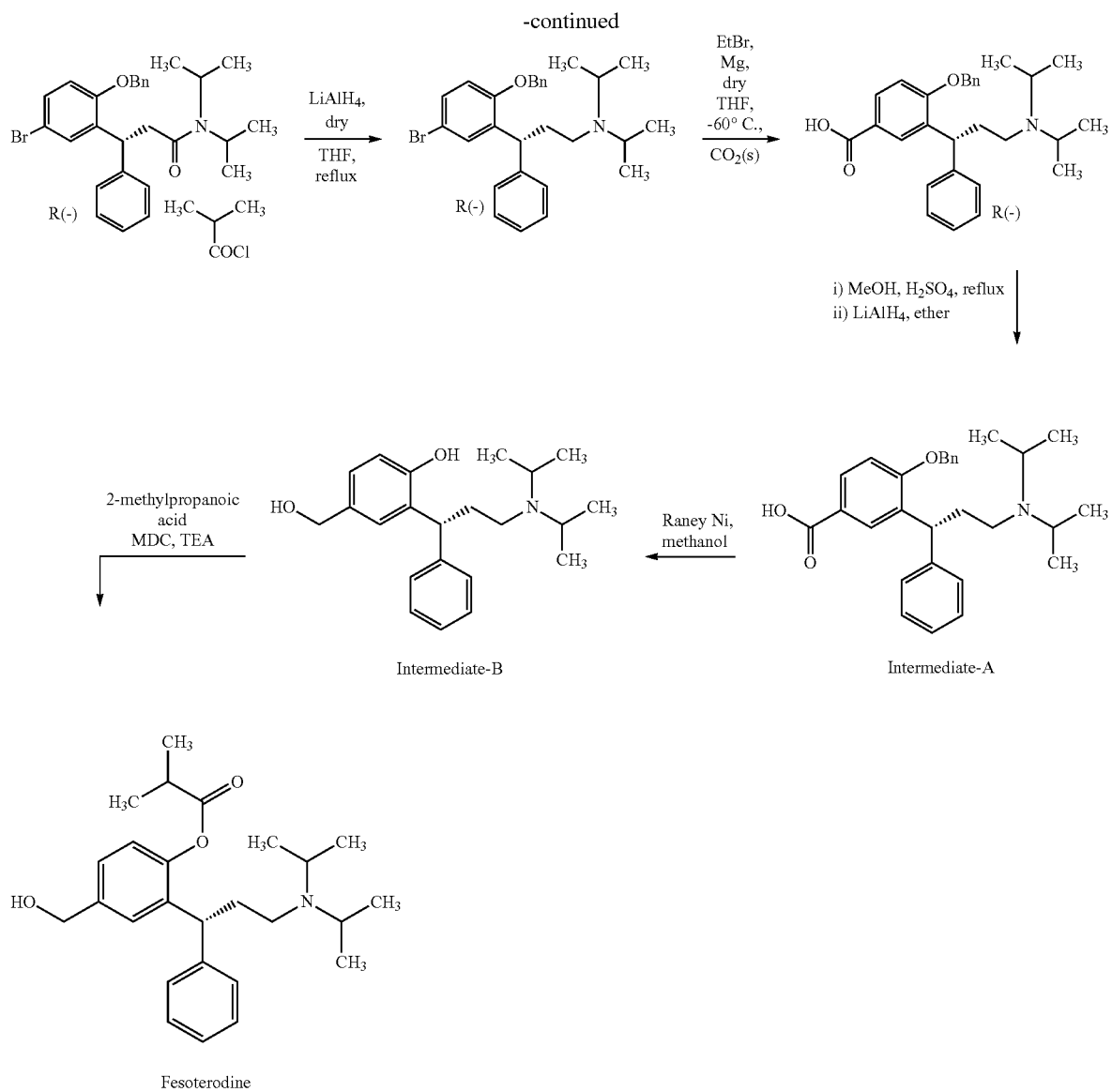

The above processes for preparation of Fesoterodine require many number of steps and involve unfriendly reagents. The process is less economical, relatively less safe and time-consuming. Hence such technology is not readily suitable for commercial production.

WO2005012227 describes process for preparation of Fesoterodine from Tolterodine. But, This process involves preparation of resolved Tolterodine and then its benzylation increase the number of steps such as debenzylation to prepare tolterodine, resolution of tolterodine and then further benzylation to convert in R(+)benzyl tolterodine. Which further convert in to Fesoterodine.

Based on the aforementioned drawbacks, prior art processes find to be unsuitable for preparation of Fesoterodine at lab scale and commercial scale operations. Hence, a need still remains for an improved and commercially viable process of preparing pure Fesoterodine or a pharmaceutically acceptable salt thereof that will solve the aforesaid problems associated with process described in the prior art and will be suitable for large-scale preparation, in lesser reaction time, in terms of simplicity, purity and yield of the product.

SUMMARY OF THE INVENTION

The present inventors have focused on the problems associated with the prior art process and has developed an improved process for the preparation of Fesoterodine, a metabolite of Tolterodine.

As a whole, a process such as the one provided by the present invention has the advantage of considerably reducing the number of synthetic steps with respect to the processes of the state of the art, while at the same time high yields are achieved with very simple steps. Likewise, said process is not toxic and allows starting from inexpensive and non-hazardous reactants, providing 3,3-diphenylpropylamines, and, particularly, Fesoterodine, with a good yield and pharmaceutical quality. All of this contributes to reducing the overall cost of the process, making it commercially interesting and allowing it to be put into practice on an industrial level.

Therefore, in one aspect the present invention provides a process for preparing Fesoterodine or its enantiomer, or a salt thereof, comprising a step of obtaining a compound of formula IV(a) or formula IV(b) or a salt there of,

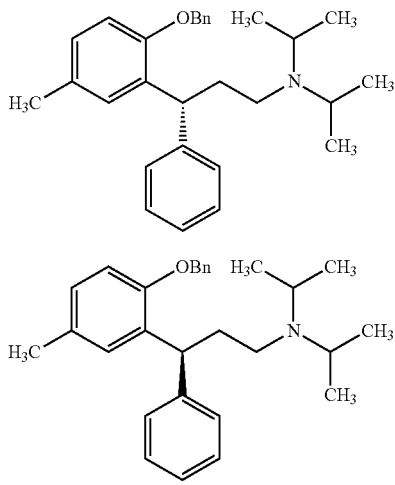

Wherein Bn is benzyl group, by the resolution of the corresponding racemic compound of formula (III):

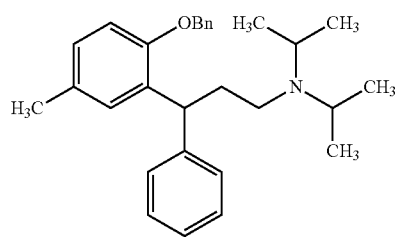

The present inventors develop a new process which involves resolution of racemic benzyl tolterodine to R(+) benzyl tolterodine that further convert in to fesoterodine. A present inventor's process reduces steps such as debenzylation to prepare tolterodine, resolution of tolterodine and then further benzylation to convert in R(+)benzyl tolterodine.

In another aspect the present invention provides a novel compound of formula VII,

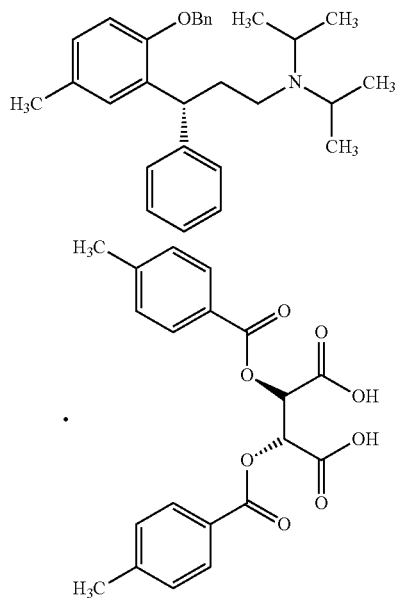

Wherein Bn is benzyl group.

In another additional aspect the present invention also provides a fumarate salt of R(+)-[4-benzyloxy-3-(3-diisopropylamino-1-phenylpropyl)-phenyl]-methanol.

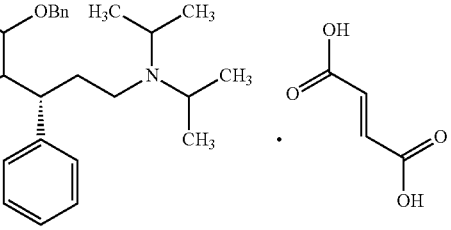

As a whole, a process such as the one provided by this invention relates to improved process for the preparation of fesoterodine and pharmaceutically acceptable salts thereof which involves use and preparation of R(+)benzyl tolterodine and fumarate salt of R(+)-[4-benzyloxy-3-(3-diisopropylamino-1-phenylpropyl)-phenyl]-methanol. The present inventors have surprisingly found that employing intermediates of the present invention in the process for the preparation of Fesoterodine, overcomes the drawbacks of the prior art and may be prepared and subsequently converted to Fesoterodine in high yield and purity.

DETAILED DESCRIPTION OF THE INVENTION

The present invention provides a process for preparation of fesoterodine or a pharmaceutically acceptable salt there of, which comprises: Reacting N,N-diisopropyl-3-(2-benzyloxy-5-methylphenyl)-3-phenyl-propane amide of formula (II) with reducing agent such as sodium borohydride, potassium borohydride and sodium cyano borohydride in the presence of a lewis acid such as aluminium chloride, calcium chloride, boron trifluoride and zinc chloride to give N,N-diisopropyl-3-(2-benzyloxy-5-methylphenyl)-3-phenyl propane amine of formula (III);

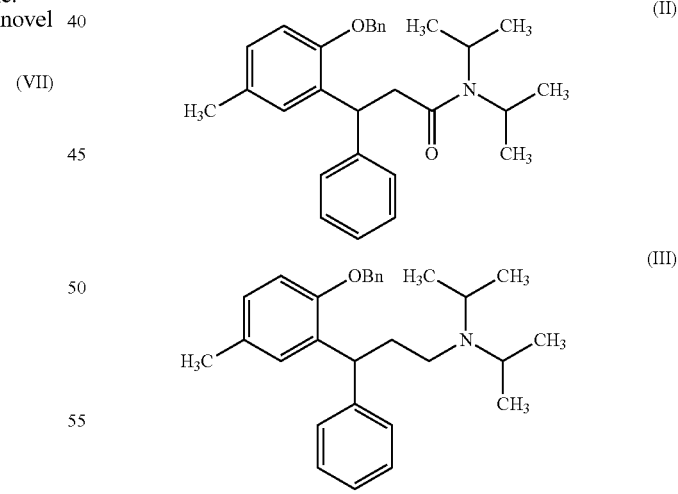

An embodiment of the present invention provides a process for the preparation of N,N-diisopropyl-3-(2-benzyloxy-5-methylphenyl)-3-phenyl propane amine of formula (III)

Another embodiment of the present invention provides a process for resolving compound of formula (III) using a suitable optically active acid such as (+) tartaric acid, (−) tartaric acid, (+) 2,3-dibenzoyl-D-tartaric acid, (−) 2,3-dibenzoyl-L-tartaric acid, mandelic acid, 3-chloro mendalic acid, abietic acid, S-(+)-camphorsulfonic acid, di-p-tolyl-D-tartaric acid and di-p-tolyl-L-tartaric acid to give (R) N,N-diisopropyl-3-(2-benzyloxy-5-methylphenyl)-3-phenyl propane amine of formula IV(a);

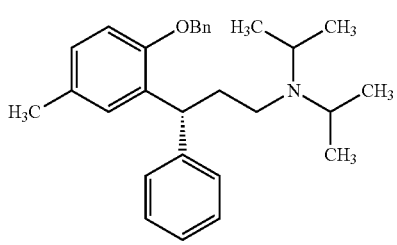

IV (a)

In another embodiment of the present invention provides a novel compound of formula VII and process for preparation of this compound.

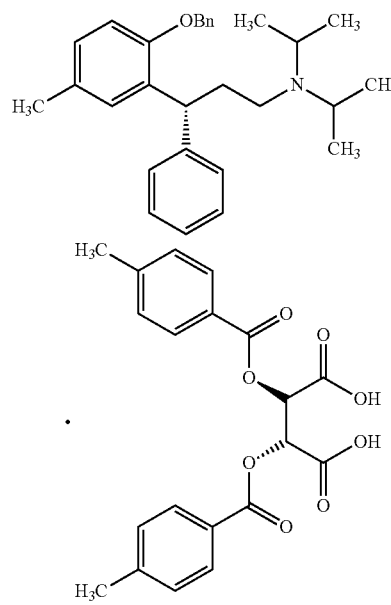

(VII)

The process for converting compound of formula IV (a) to R-(+)-[4-benzyloxy-3-(3-diisopropylamino-1-phenyl-propyl)-phenyl]-methanol of formula (V) involves oxidation of methyl group using oxidizing agent such as ruthenium chloride/sodium periodate, fuming nitric acid, peracids, Dess-Martin reagent, chromium 4-oxide, nickel peroxide, sodium dichromate, manganese dioxide, potassium permanganate, activated silver oxide, pyridinium chlorochromate, ceric ammonium nitrate or ceric ammonium citrate. Then reduction of aldehyde group is carried out using reducing agent such as sodium borohydride, potassium borohydride, Vitride, tetralkylammonium borohydride, calcium borohydride, zinc borohydride, sodium cyanoborohydride, lithium aluminium hydride or mixtures thereof.

Debenzylating compound of formula (V) using hydrogenation catalyst such as Raney Nickel, palladium on carbon, palladium acetate, platinum oxide, platinum black, platinum oxide adsorbed on carbon, rhodium on carbon, ruthenium and its salts adsorbed on solid support to obtain R-(+)-[4-hydroxy-3-(3-diisopropylamino-1-phenyl-propyl)-phenyl]-methanol of formula (VI);

Condensing the compound of formula (VI) with isobutyryl chloride in a suitable solvent, optionally in the presence of a suitable base, to produce substantially pure fesoterodine and optionally converting the fesoterodine formed in to a physiologically acceptable acid addition salt of fesoterodine.

In yet another object of the present invention provides a resolution process for the preparation of (R)—N,N-diisopropyl-3-(2-(benzyloxy-5-halophenyl)-3-phenylpropyl amine compound of formula IV(a) or a salt thereof, which comprises: reacting racemic (±)N,N-diisopropyl-3-(2-(benzyloxy-5-halophenyl)-3-phenylpropylamine of formula III; with a di-p-tolyl-D-tartaric acid in a mixture of water and isopropanol, to produce a diastereomeric excess of di-p-tolyl-D-tartaric acid salt of compound of formula VII. Separating the diastereomers of formula VII; and neutralizing the separated diastereomers with a base in a suitable solvent to provide enantiomerically pure compound of formula IV(a).

In an embodiment of the present invention provides an acid addition salt of a compound of formula V; comprising said compound of formula V and an acid selected from hydrochloric acid, hydrobromic acid, sulfuric acid, methanesulfonic acid, phosphoric acid, nitric acid, benzoic acid, citric acid, tartaric acid, fumaric acid or malic acid.

In an embodiment of the present invention provides a novel compound a compound of formula

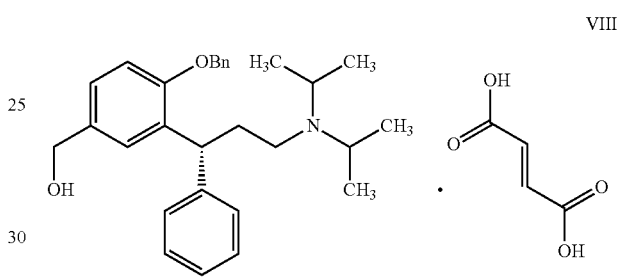

VIII

In yet another embodiment of the present invention provides a process for preparation of fesoterodine or it's a physiologically acceptable salt comprising the use of fumarate salt of compound of formula VIII.

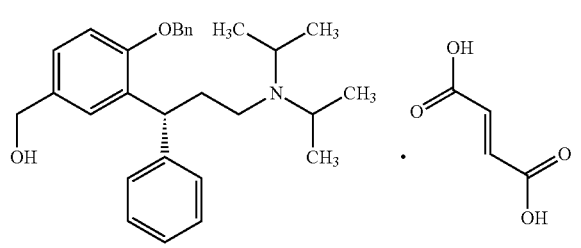

VIII

In yet another embodiment of the present invention provides a process for preparation of fesoterodine or it's a physiologically acceptable salt comprises a step of crystallizing the compound of formula II in isopropanol.

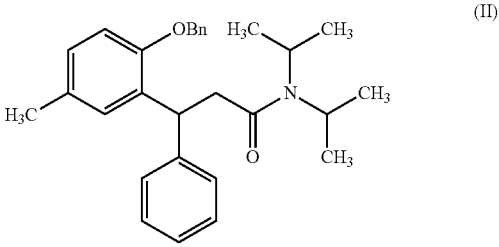 [SMILES: Cc1ccc(OCc2ccccc2)c(C(CC(=O)N(C(C)C)C(C)C)c2ccccc2)c1]

(II)

In another embodiment of the present invention provides a solid form of N,N-diisopropyl-3-(2-benzyloxy-5-methylphenyl)-3-phenyl propane amide.

The embodiments of present invention are shown in below given scheme.
The process for preparation of Fesoterodine fumarate is shown in the scheme III.
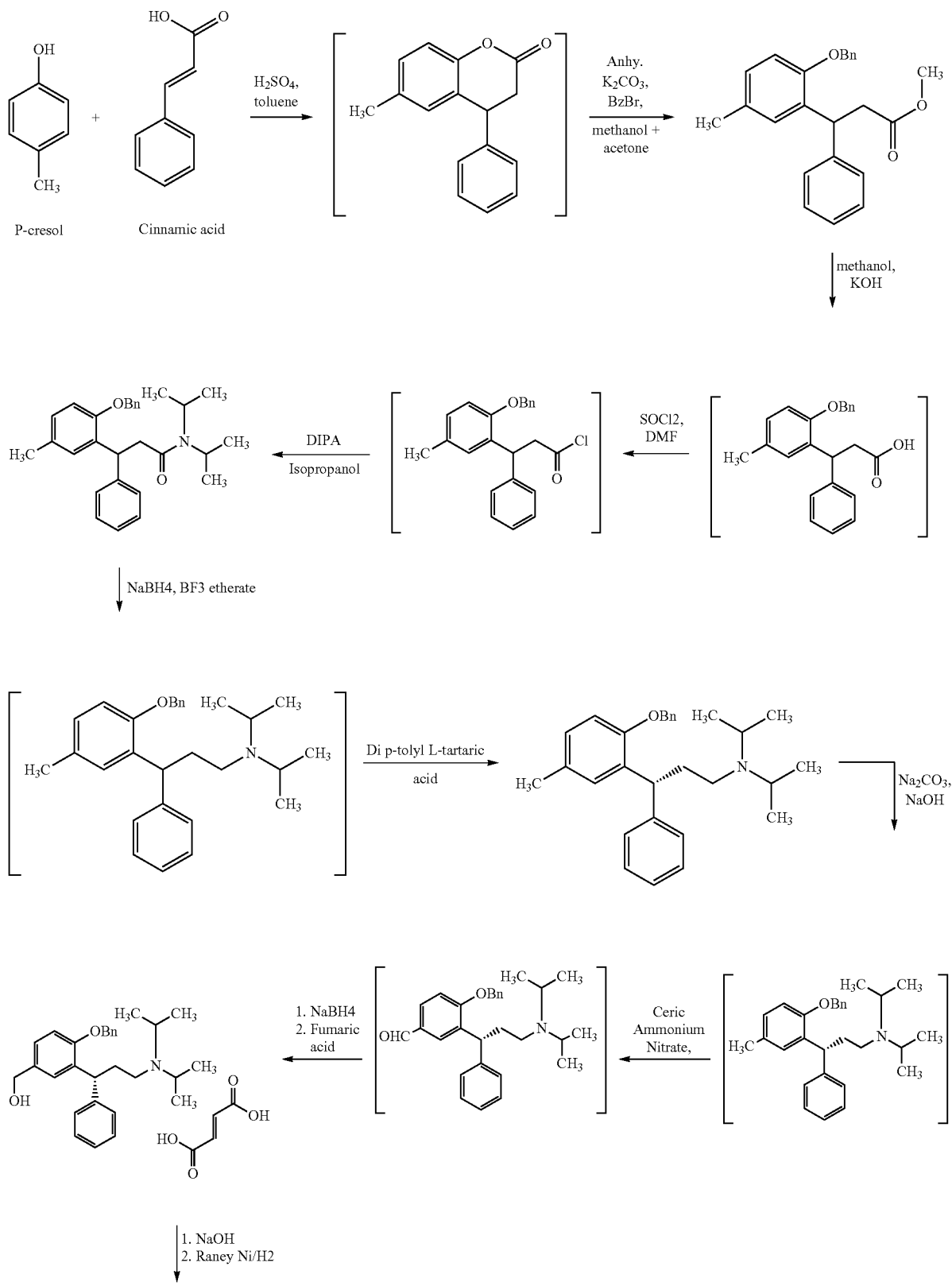
Scheme-III -continued

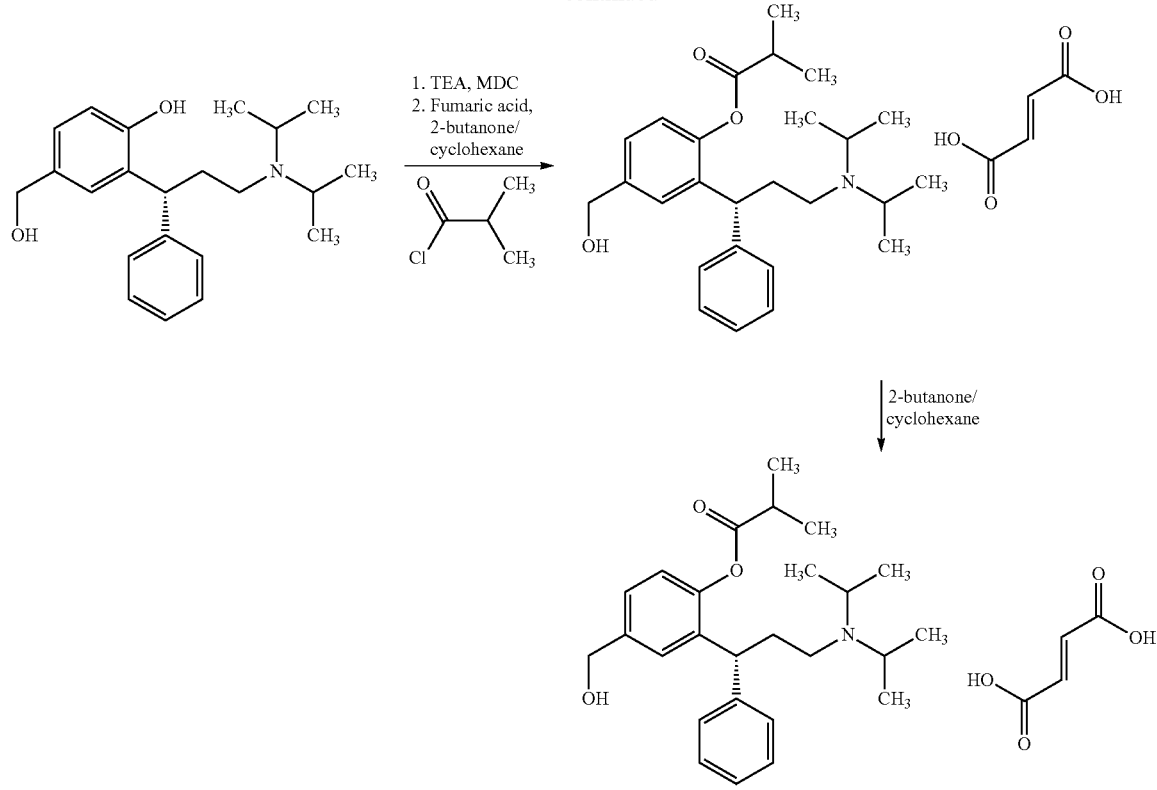

The present invention further illustrated in detail by the below examples which are however not limit to the scope of the invention.

EXAMPLES

Example-1

Preparation of methyl 3-(2-benzyloxy-5-methyl-phenyl)-3-phenyl propionate

Trans-cinammic acid (1.0 Kg) was added to a 1 L 4-neck round bottom flask equipped with a mechanical stirrer, thermocouple, and nitrogen inlet. Para-cresol (0.766 Kg) was preheated in a water bath at 60° C. and added to the cinammic acid (II) followed by concentrated sulfuric acid (13.0 mL, 243 mmol). The reaction was immediately heated to a set point of 127° C. and stirred at 120° C.-125° C. for 6-7 hours. When the reaction was complete the mixture was cooled to 90° C. and toluene (3.0 L) and water (0.5 L) are added to the crude product. The layers are separated and the organic layer was concentrated under reduced pressure. Methanol (1.0 L) was added and distillation is continued to give 3,4-dihydro-6-methyl-4-phenyl-2H-benzopyran-2-one as oily mass.

Benzyl bromide (1.372 Kg), potassium carbonate (1.275 Kg), acetone (5.0 L) and methanol (5.0 L) were loaded in to the mixture. The contents were heated to reflux temperature for about 4-5 hours and then distilled off the solvent from the reaction mass. 13 L of water was added to the residue and extracted the solution twice with ethyl acetate (5.0 L). Combined organic layers and distilled the solvent completely under vacuum. Methanol (5.3 L) was added to the residue and heated for 30 to 45 min at 55±5° C. to get clear solution, then stirred the solution at 0-5° C. for about 2 hours. The formed solid was filtered and washed with methanol (1.6 L) and the material was dried to give 1.8 kg of methyl 3-(2-benzyloxy-5-methyl-phenyl)-3-phenyl propionate. Yield 74%.

Example-2

Preparation of N,N-diisopropyl-3-(2-benzyloxy-5-methyl-phenyl)-3-phenyl propane amide (II)

Methyl 3-(2-benzyloxy-5-methyl-phenyl)-3-phenyl propionate (1.0 kg) was dissolved in Methanol (4.0 L) to a 1 L 4-neck round bottom flask equipped with a mechanical stirrer, thermocouple, and nitrogen inlet. The solution of Potassium hydroxide (0.232 Kg) in Process water (0.550 L) was added and refluxed reaction mixture for 3 to 4 hours. After completion of the reaction solvent was distilled out and stirred the reaction mass with Process water (3.6 L) and Dichloromethane (4.0 L). Then adjusted the pH to 1-2 using conc. HCl (0.5-0.8 L). Separated organic layer and distilled out solvent completely to give oil.

Toluene (3.0 L), Dimethylformamide (0.01 L) and Thionyl chloride (0.411 Kg) were added in reaction mass and heated the reaction mass at 62±3° C. for 2-3 hours. After completion of reaction distilled Toluene completely and again charged Toluene (3.0 L) into the residue below 60° C. and cooled the reaction mass to 2±3° C. Meanwhile prepared solution of Diisopropylamine (0.70 Kg) in Toluene (3.0 L) and added slowly into the reaction mass at 5±5° C. Stirred the reaction mass for 3-4 hrs at 30±5° C. Process water (5.0 L) was added and separated out the organic layer. Distilled out Toluene completely under vacuum and charged Isopropyl alcohol (1.0 L) that also distilled under vacuum below 60° C. and again Isopropyl alcohol (4.0 L) was added to the residue. Heated to 55±5° C. to get clear solution and then cooled the mass to 2±3° C. Filtered the solid under nitrogen atmosphere and washed with chilled Isopropyl alcohol. The material was dried under vacuum to obtain 0.98 Kg solid N,N-diisopropyl-3-(2-benzyloxy-5-methyl-phenyl)-3-phenyl propane amide. Yield 82%.

Example-3

Preparation of R-(+)-N,N-diisopropyl-3-(2-benzyloxy-5-methylphenyl)-3-phenyl propane amine Di-p-toluoyl L-tartaric acid salt (VII)

N,N-diisopropyl-3-(2-benzyloxy-5-methyl-phenyl)-3-phenyl propane amide (1.0 Kg,), Tetrahydrofuran (5.0 lit) and Sodium borohydride (0.43 Kg) were taken into the round bottom flask. The contents were cooled to 2±3° C. followed by drop wise addition of Borontrifluoride etherate (1.93 Kg). The reaction mixture was stirred for 10-12 hrs at 33±2° C. After completion of the reaction a solution of Conc. Hydrochloric acid (2.83 L) into Process water (2.83 L) was added to the reaction mass at 40±10° C. and stirred for 2-3 hrs at 62±3° C. The product was extracted in dichloromethane (4.0 L). Dichloromethane distilled out completely under vacuum below 50° C. This was followed by addition of Isopropyl alcohol (1.0 L) and distilled it completely to give (±) N,N-diisopropyl-3-(2-benzyloxy-5-methylphenyl)-3-phenyl propane amine.

Isopropyl alcohol (8.0 L), water (0.8 L) and Di-p-toluoyl-L-tartaric acid (0.901 Kg) was added in reaction mixture and refluxed for 50-60 min. Gradually cooled the reaction mass at 32±3° C. within 5-6 hrs and Stirred it for 2.0-3.0 hrs. Filtered the solid and washed with Isopropyl alcohol (1.11 L). Obtain solid was recrystallized several times in Isopropyl alcohol and water to give 0.64 Kg R-(+)-N,N-diisopropyl-3-(2-benzyloxy-5-methylphenyl)-3-phenyl propane amine Di-p-toluoyl L-tartaric acid salt. Yield 34%.

$^1$H NMR (CDCl$_3$) 300 mHz δ (ppm): 1.10-1.21 (12H, m); 2.10-2.32 (9H, d); 2.43-2.59 (2H, m); 2.59-2.76 (2H, m); 4.21-4.26 (1H, t); 4.96 (2H, s); 5.91 (2H, s); 6.77-6.80 (1H, d); 6.94-6.95 (1H, dd); 7.06-7.09 (5H, d); 7.17-7.38 (10H, m); 7.85-7.88 (4H, d). IR: 2966, 1719, 1704, 1611, 1499, 1246.

Example-4

Preparation of R(+)-[4-benzyloxy-3-(3-diisopropylamino-1-phenyl-propyl)-phenyl]-methanol fumarate salt (VIII)

R-(+)-N,N-diisopropyl-3-(2-benzyloxy-5-methylphenyl)-3-phenyl propane amine Di-p-toluoyl L-tartaric acid salt (100 g), Dichloromethane (400 ml) and process water (300 ml) were added in RB Flask. Followed by addition of a solution of sodium carbonate (50 g) in Process water (500 ml) and stirred for 25-30 min. Separated out organic layer and distilled out Dichloromethane to give amine. Charged Acetonitrile (500 ml) and Process water (250 ml) into the reaction mass and cooled the reaction mass to 5±3° C. Slowly added solution of Ceric ammonium nitrate (230 g) in Process water (250 ml). The contents were stirred at 17±3° C. for 3-4 hrs followed by lot wise addition of Sodium Borohydride (71 g) at 5±3° C. Conc. Hydrochloric acid was added and stirred the reaction mass for 90-120 min at 35±3° C. The product was extracted in Dichloromethane (200 ml) and distilled out Dichloromethane completely to give oily mass. Dichloromethane (450 ml) and Fumaric acid (20.54 g) were added to Oily mass and heated it to reflux. Cooled the solution and filtered the solid to 65.0 g give R-(+)-[4-benzyloxy-3-(3-diisopropylamino-1-phenyl-propyl)-phenyl]-methanol fumarate salt.

Yield 95%.

$^1$H NMR (CDCl$_3$) 300 mHz δ (ppm): 1.20-1.21 (12H, d), 2.43-2.5 (2H, m), 2.96-3.02 (2H, m), 3.59-3.66 (2H, m), 4.42-4.44 (1H, t), 4.53 (2H, s), 5.04-5.08 (2H, s), 6.80 (2H, s), 7.00-7.32 (13H, m), IR: 3419, 3027, 2994, 2874, 1703, 1611, 1500, 1246.

Example-5

Preparation of R(+)-2-(3-diisopropylamino-1-phenylpropyl)-hydroxymethyl phenol

R-(+)-[4-benzyloxy-3-(3-diisopropylamino-1-phenyl-propyl)-phenyl]-methanol fumarate salt (100 g), Dichloromethane (400 ml), Process water (200 ml) and solution of sodium carbonate (50 g) in Process water (500 ml) were stirred in round bottom flask. Followed by addition of Sodium hydroxide (3.2 g) into the reaction mass and stirred it for 25-30 min. The organic layer was separated and distilled out Dichloromethane completely to give R-(+)-[4-benzyloxy-3-(3-diisopropylamino-1-phenyl-propyl)-phenyl]-methanol. The obtain oil, Raney Nickel (30 g) and Methanol (100 ml) were taken in to a hydrogenator and Maintained 4-5 Kg/Cm$^2$ pressure of Hydrogen for 30-60 min. The mixture was then filtered and the solvent was removed by vacuum at below 50° C. This was crystallized in ethyl acetate (60 ml) to give 37.0 g R-(+)-[4-hydroxy-3-(3-diisopropylamino-1-phenyl-propyl)-phenyl]-methanol. Yield 59%.

Example-6

Preparation R-(+)-2-(3-Diisopropylamino-1-phenyl-propyl)-4-hydroxymethylphenylisobutyrate ester A solution of R-(+)-2-(3-diisopropylamino-1-phenylpropyl)-4-hydroxymethylphenol (65.0 g) and triethylamine (20.4 g) in 750 ml dichloromethane has a solution of isobutyrate chloride (23.4 g) in 250 ml dichloromethane added under agitation and cooling. Following addition agitation takes place for a further 15 minutes at 0° C., then for 30 minutes at room temperature and then one after another washing with water (250 ml) and 5% aqueous sodium hydrogen carbonate solution. The organic phase is separated and concentrated on the rotary evaporator until dry. The ester R-(+)-2-(3-diisopropylamino-1-phenylpropyl)-4-hydroxymethylphenylisobutyrate ester is obtained as colourless, viscous oil; yield: 77.1 g.

Example-7

Preparation of R-(+)-2-(3-Diisopropylamino-1-phenylpropyl)-4-hydroxymethylphenylisobutyrate ester hydrogen fumarate A solution of 41.87 g (102 mmol) R-(+)-2-(3-diisopropylamino-1-phenylpropyl)-4-hydroxymethylphenylisobutyrate ester in 90 ml 2-butanone has fumaric acid (11.81 g, 102 mmol) added while heating. Following dissolution of the acid, cyclohexane (20-30 ml) is slowly added under agitation until the onset of turbidity. The colourless, homogenous deposit is initially left for 18 hours at room temperature, and then for several hours at 0[deg.] C. The colourless crystals that have precipitated are sucked off, washed with a little cyclohexane/2-butanone (90:10, vol.-%) and dried in the vacuum at 30[deg.] C. 44.6 g (83.1% of theoretical) hydrogen fumarate salt of R-(+)-2-(3-diisopropylamino-1-phenylpropyl)-4-hydroxymethylphenyl-isobutyrate ester is obtained.

The invention claimed is:
1. A process for preparing Fesoterodine or its enantiomer, or a salt thereof, comprising:
   obtaining a compound of formula IV(a) or formula IV(b) or a salt there of,

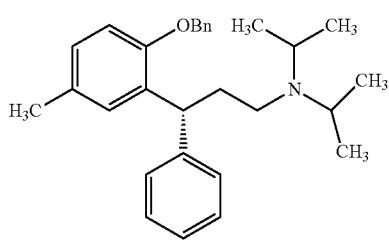

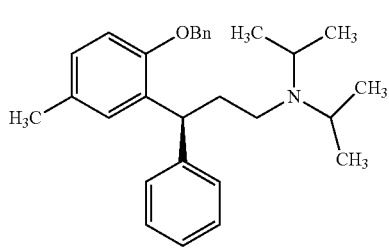

wherein Bn is benzyl group, by the resolution of the corresponding racemic compound of formula (III):

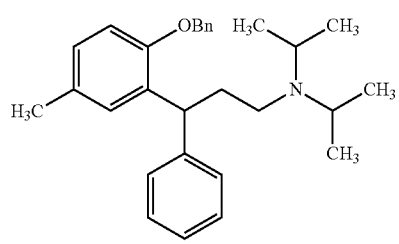

wherein resolution of racemic compound of formula (III) through formation of the diastereomeric salt thereof with an optically active acid; and
preparing Fesoterodine or its enantiomer from compounds IV(a) or IV(b) or a salt thereof.

2. A process according to claim 1, wherein the optically active acid, is selected from an optically active carboxylic acid or sulphonic acid.

3. A process according to claim 2, wherein an optically active acid is selected from (+) tartaric acid, (−) tartaric acid, (+) 2,3-dibenzoyl-D-tartaric acid, (−) 2,3-dibenzoyl-L-tartaric acid, mandelic acid, 3-chloro mendalic acid, abietic acid, S-(+)-camphorsulfonic acid, di-p-tolyl-D-tartaric acid and di-p-tolyl-L-tartaric acid.

4. A process according to claim 1, wherein the resolution of racemic compound of formula (III) is carried out in a solvent selected from water, a dipolar aprotic solvent, a C3-C8 ketone, a cyclic or acyclic ether, an ester, a chlorinated solvent and a polar protic solvent, or a mixture of two or more, typically two, of said solvents.

5. A process for preparation of fesoterodine of formula (I)

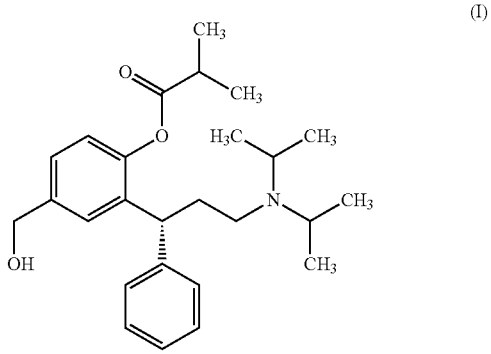 [SMILES: CC(C)C(=O)Oc1ccc(CO)cc1[C@H](CCN(C(C)C)C(C)C)c1ccccc1]

or a pharmaceutically acceptable salt there of, characterized by the steps of:
   a. reacting N, N-diisopropyl-3-(2-benzyloxy-5-methylphenyl)-3-phenyl-propane amide of formula (II) with reducing agent in the presence of a lewis acid to give N, N-diisopropyl-3-(2-benzyloxy-5-methylphenyl)-3-phenyl propane amine of formula (III);

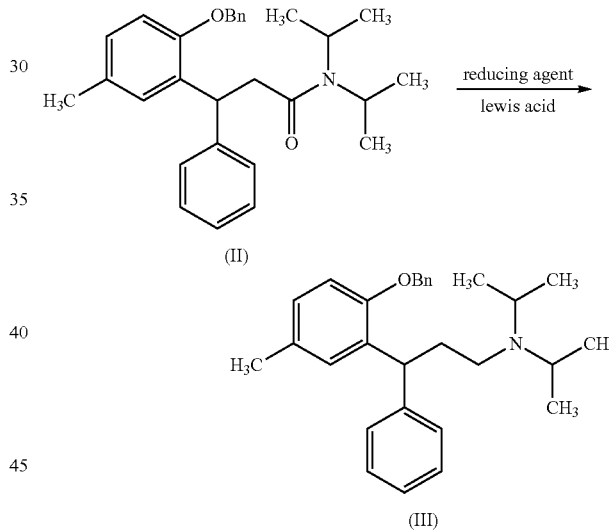

wherein Bn is benzyl group
   b. resolving compound of formula (III) using a suitable optically active acid to give (R) N, N-diisopropyl-3-(2-benzyloxy-5-methylphenyl)-3-phenyl propane amine of formula IV(a);

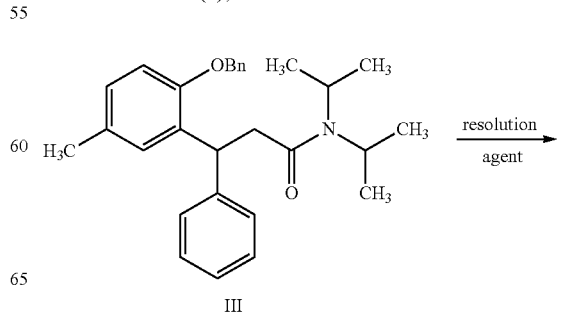

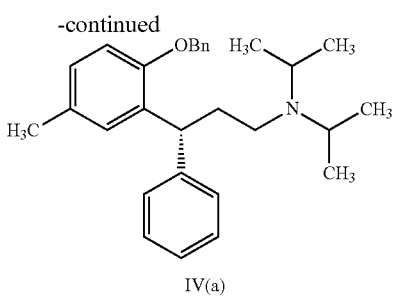

IV(a)

c. converting compound of formula IV(a) to R-(+)-[4-benzyloxy-3-(3-diisopropylamino-1-phenyl-propyl)-phenyl]-methanol of formula (V);

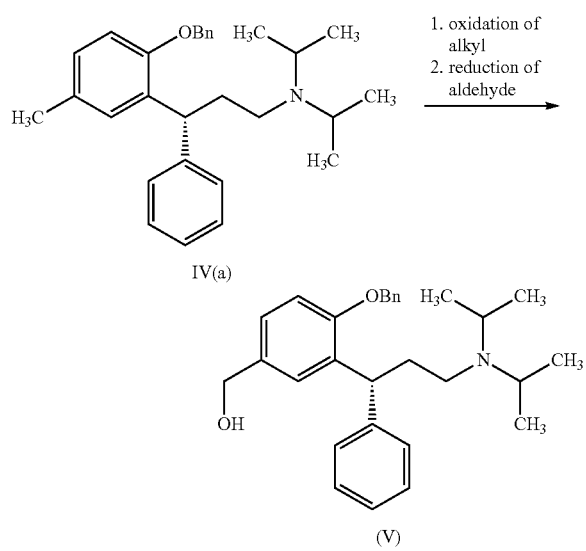

d. debenzylating compound of formula (V) using hydrogenation to obtain R-(+)-[4-hydroxy-3-(3-diisopropylamino-1-phenyl-propyl)-phenyl]-methanol of formula (VI); and

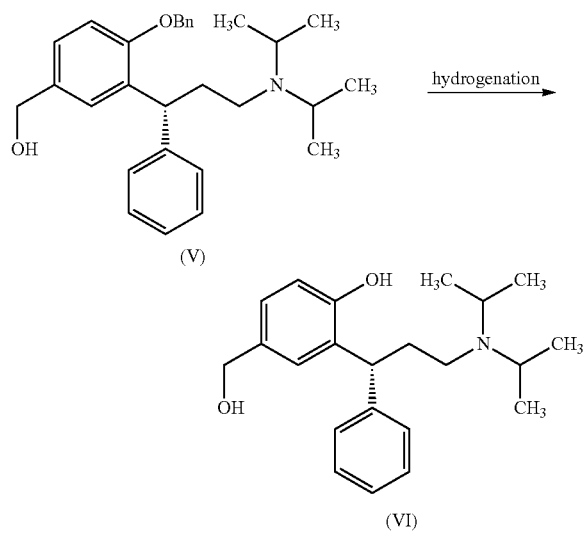

e. condensing the compound of formula (VI) with isobutyryl chloride in a suitable solvent, optionally in the presence of a suitable base, to produce substantially pure fesoterodine and optionally converting the fesoterodine formed in to a physiologically acceptable acid addition salt of fesoterodine.

6. The process of claim 5, wherein the reducing agent used in step (a) is a metal hydride, with the proviso that the metal hydride does not include lithium aluminium hydride, selected from the group comprising sodium borohydride, potassium borohydride and sodium cyano borohydride; wherein the lewis acid is selected from the group comprising aluminium chloride, calcium chloride, boron trifluoride and zinc chloride.

7. The process of claim 5, wherein the resolution agent used in step (b) is selected from (+) tartaric acid, (−) tartaric acid, (+) 2,3-dibenzoyl-D-tartaric acid, (−) 2,3-dibenzoyl-L-tartaric acid, mandelic acid, 3-chloro mendalic acid, abietic acid, S-(+)-camphorsulfonic acid, di-p-tolyl-D-tartaric acid and di-p-tolyl-L-tartaric acid.

8. The process of claim 5, wherein the oxidizing agent used in step (c) is selected from the group consisting of ruthenium chloride/sodium periodate, fuming nitric acid, peracids, Dess-Martin reagent, chromium 4-oxide, nickel peroxide, sodium dichromate, manganese dioxide, potassium permanganate, activated silver oxide, pyridinium chlorochromate, ceric ammonium nitrate or ceric ammonium citrate.

9. The process of claim 5, wherein the reducing agent used in step (c) is selected from the group consisting of sodium borohydride, potassium borohydride, Vitride, tetralkylammonium borohydride, calcium borohydride, zinc borohydride, sodium cyanoborohydride, lithium aluminum hydride or mixtures thereof.

10. The process of claim 5, wherein the debenzylation is carried out by hydrogenation of compound of formula (V) by using a hydrogen gas and hydrogenation catalyst selected from Raney Ni, palladium on carbon, palladium acetate, platinum oxide, platinum black, platinum oxide adsorbed on carbon, rhodium on carbon, ruthenium and its salts adsorbed on solid support.

11. A process according to claim 1, wherein the resolution of racemic compound of formula (III) is carried out in isopropyl alcohol.

12. A process according to claim 6, wherein the reducing agent used in step (a) is sodium borohydride and the lewis acid is boron trifluoride.

13. A process according to claim 7, wherein the resolution agent used in step (b) is di-p-tolyl-D-tartaric acid.

14. A process according to claim 8, wherein the oxidizing agent used in step (c) is ceric ammonium nitrate.

15. A process according to claim 9, wherein the reducing agent used in step (c) is sodium borohydride.

16. A process according to claim 10, wherein the debenzylation is carried out by hydrogenation of compound of formula (V) by using a hydrogen gas and Raney Ni as the hydrogenation catalyst.

* * * * *